United States Patent [19]

Weeks

[11] Patent Number: 4,645,492
[45] Date of Patent: Feb. 24, 1987

[54] CATHETER ANCHORING DEVICE

[75] Inventor: Vaughan B. Weeks, Racine, Wis.

[73] Assignee: Medical Engineering Corporation, Racine, Wis.

[21] Appl. No.: 830,917

[22] Filed: Feb. 19, 1986

Related U.S. Application Data

[63] Continuation of Ser. No. 540,466, Oct. 11, 1983, abandoned.

[51] Int. Cl.⁴ .............................................. A61M 5/32
[52] U.S. Cl. .................................... 604/174; 604/180; 128/DIG. 26
[58] Field of Search ........................ 604/174, 178–180; 128/DIG. 26, 640

[56] References Cited

U.S. PATENT DOCUMENTS

| | | | |
|---|---|---|---|
| 2,586,940 | 10/1947 | Graham | 128/DIG. 26 |
| 3,683,911 | 8/1972 | McCormick | 128/DIG. 26 |
| 3,856,020 | 12/1974 | Kovac | 604/177 |
| 4,235,234 | 11/1980 | Whitney et al. | 604/177 |
| 4,392,857 | 7/1983 | Beran | 604/179 |
| 4,435,174 | 3/1984 | Redmond et al. | 604/174 |
| 4,437,463 | 3/1984 | Ackerman | 604/179 |
| 4,579,120 | 4/1986 | MacGregor | 604/180 |

FOREIGN PATENT DOCUMENTS 2147811  5/1985  United Kingdom ............... 604/180

OTHER PUBLICATIONS

Technical Note, Tegtmeyer.

Primary Examiner—Stephen C. Pellegrino
Assistant Examiner—Mark Rooney
Attorney, Agent, or Firm—Stuart E. Krieger

[57] ABSTRACT

A device for anchoring catheter tubing to the skin of a patient which includes a resiliently flexible pad attachable to the patient's skin. The pad has a predetermined dimensioned arcuate passageway disposed therein for snugly receiving and redirecting the tube. The passageway is externally accessible along its length by manually spreading the pad along a slit.

4 Claims, 6 Drawing Figures

CATHETER ANCHORING DEVICE

This is a continuing application of application Ser. No. 540,466 filed Oct. 11, 1983, now abandoned.

DESCRIPTION

Field of the Invention

The present invention relates to medical device and more particularly to a device for anchoring catheter tubing or the like to the skin of a patient.

BACKGROUND OF THE INVENTION

It is frequently necessary during the medical treatment of a patient in a hospital to use resilient, flexible, slender tubes known as catheters for delivery of fluid intravenously. These tubes typically extend from containers holding an infusion liquid into the patient's skin where a needle projects from the tubing into the patient's vein. Catheter tubing is also used when it is necessary to remove or drain liquid from the patient's body by suction. Relatively common surgical procedures which require drainage for a prolonged period of time include dialysis and percutaneous nephrostomy.

Proper securement of the catheter tubing during medical treatment is necessary to reduce the pain, inconvenience and possible contamination to the patient at the puncture site which can otherwise occur from dislodgement of the catheter tubing from the patient's body.

In the past, catheter tubing was commonly secured to the patient by first coiling the tube to form a loop, applying a strip of adhesive tape over the loop and attaching the opposite ends of each strip of tape to the patient's skin. The function of the loop was to unravel without disturbing the catheter or needle when unexpected tension was applied to the tubing.

More recently, devices have been developed which facilitate anchoring of catheter tubing to the patient e.g. U.S. Pat. No. 4,164,943 to J. D. Hill et al; U.S. Pat. No. 4,129,128 to R. H. McFarlane; and U.S. Pat. No. 3,918,446 to P. M. Buttaravoli.

Force connectors have also been developed which reduce or eliminate the need for loops in the tubing. In use, a force connector may be attached, for example, between the drainage container and tubing or to the anchoring device between two lengths of tubing. In the latter situation, the force connector provides fluid communication between a first length of catheter tubing extending from the drainage container to one side of the force connector and the second length of tubing extending from the other side of the connector through the anchoring device into the patient's skin. The force connector used in this instance is designed to disconnect, typically from the first length of tubing, at a predetermined tension level without disturbing the anchoring device or second length of tubing. This disconnection prevents dislodgement of the catheter and needle from the patient. For this type of force connector to operate properly, the second length of tubing must be suitably secured to the anchoring device, and the anchoring device in turn must be properly affixed to the patient's skin. When force connectors are not utilized, it is even more important that the application of force to the catheter tubing be transmitted through the anchoring device to the patient's skin to reduce the possibility of tubing dislodgement.

Besides the need for the anchoring device to be both properly attached to the patient's skin and to secure the catheter tube, it is also advantageous if the anchoring device is capable of both easy installation and removal from the catheter tube while the tube is operably attached to the patient. Furthermore, for the patient's comfort and safety, e.g. so as not to be interfered with by the patient's movement or clothing, it is desirable to redirect the tubing from the puncture site, where it leaves normal to the patient's skin, to a direction parallel to the patient's skin, without causing interference in the fluid flow by kinking or crimping of the tubing.

It is, accordingly, an object of the present invention to provide a device attachable to the patient's skin which provides a sleeve or passageway positionable around an operably positioned catheter tubing that changes the tube orientation and restrains or anchors the tubing against removal from the patient.

SUMMARY OF THE INVENTION

This object and others is achieved by a novel device for anchoring a catheter tube or the like to the skin of a patient. This device includes a resiliently flexible pad that includes a disc-like base portion with a bottom surface which is positioned subjacent to the patient's skin, a top surface having a body portion upstanding therefrom and a peripheral edge between and interconnecting the top and bottom surfaces.

The pad has an arcuate passageway extending through it which is predeterminedly dimensioned so as to snugly receive the catheter tube, with the circumferential walls surrounding the passageway acting as a sleeve for the tube. The passageway has a length which extends from a first port or opening in the base portion of the pad to a second port in the body portion.

A slit extends in the base portion from the peripheral edge to the first port and from the first port to the second port. The pad is capable of being spread manually along this slit to permit external access to the passageway for insertion of the catheter tube therein. The slit resiliently closes upon manual release of the pad whereupon the tube is frictionally restrained within the passageway.

The body portion has an annular channel grooved into its circumference that permits a cable tie to be guided therein about the body portion. Upon tightening of the tie, the slit is held closed and the passageway walls frictionally bear against the tubing so as to prevent the tubing from sliding through or from the passageway.

BRIEF DESCRIPTION OF THE DRAWINGS

The foregoing and other objects, characteristics of advantages of the present invention will be more clearly understood from the following description when read in conjunction with the accompanying drawings in which.

DESCRIPTION OF THE PREFERRED EMBODIMENT

Figure 1:
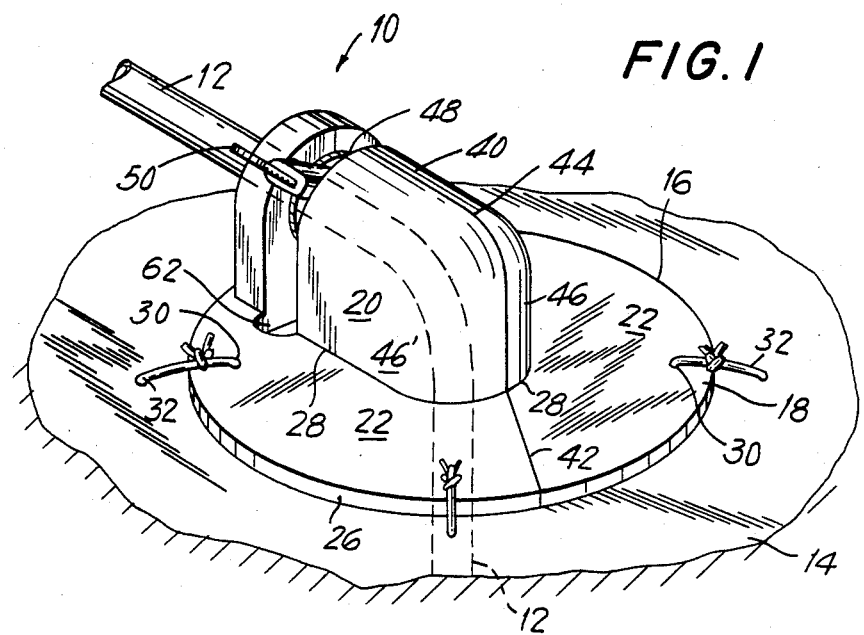
FIG. 1 is a perspective view of a catheter anchoring device in accordance with the present invention sutured to the patient's skin.
Figure 2:
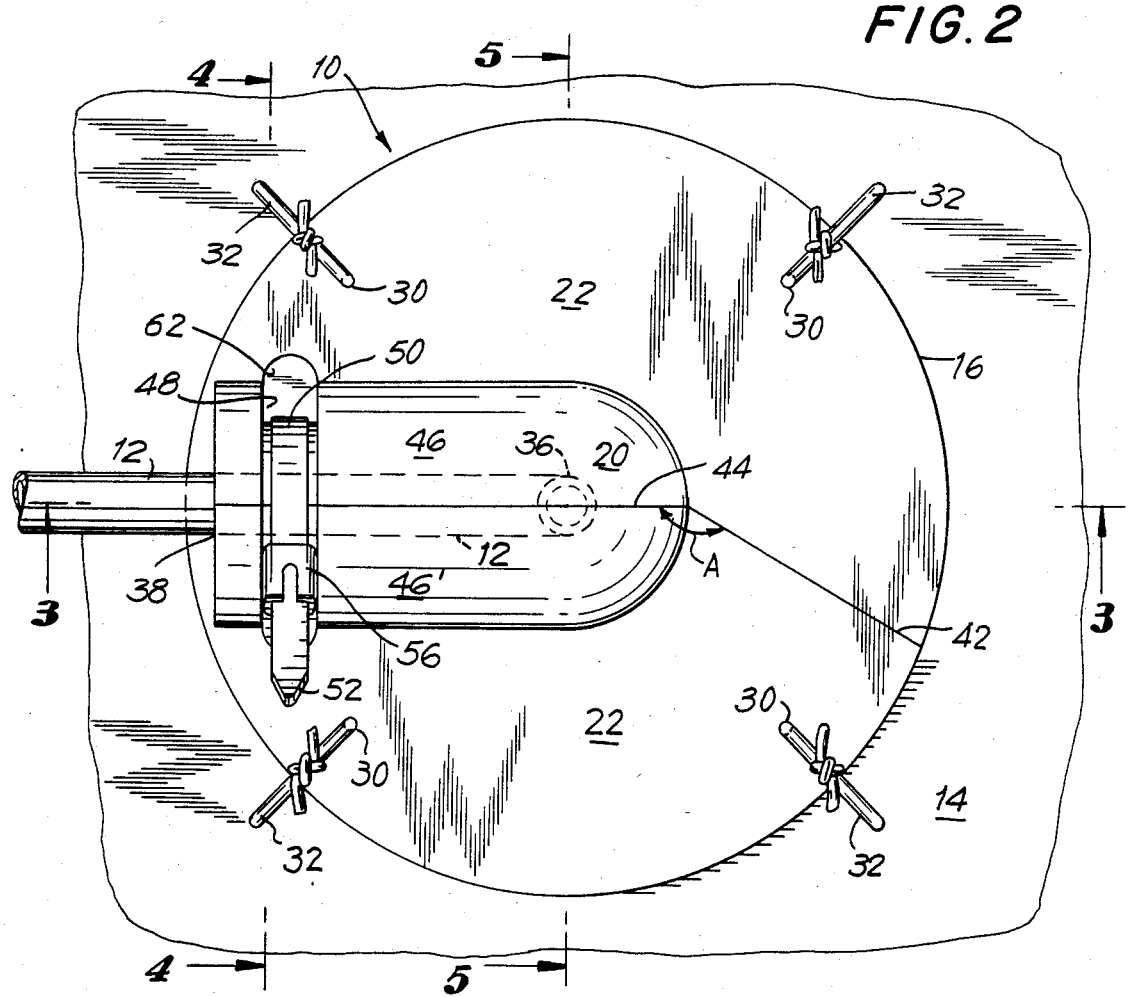
FIG. 2 is a top plan view of the device shown in FIG. 1.
Figure 3:
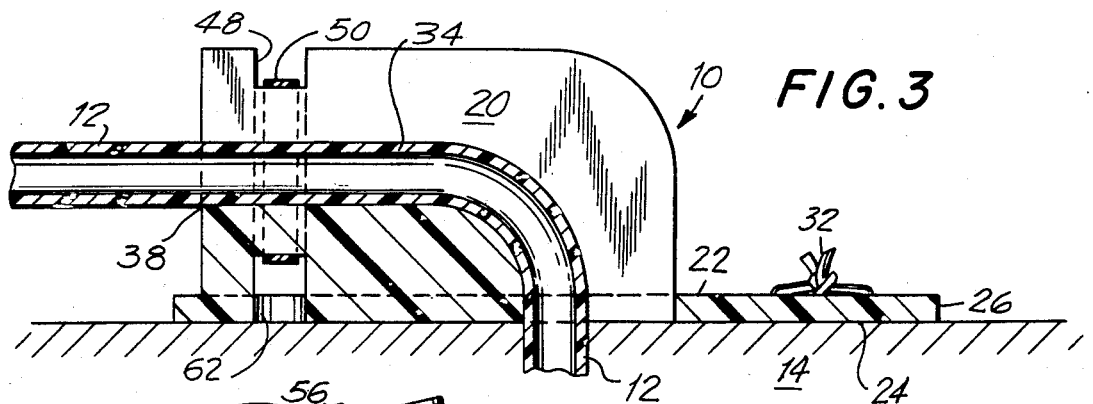
FIG. 3 is a cross-sectional view taken along line 3—3 of FIG. 2.
Figure 4:
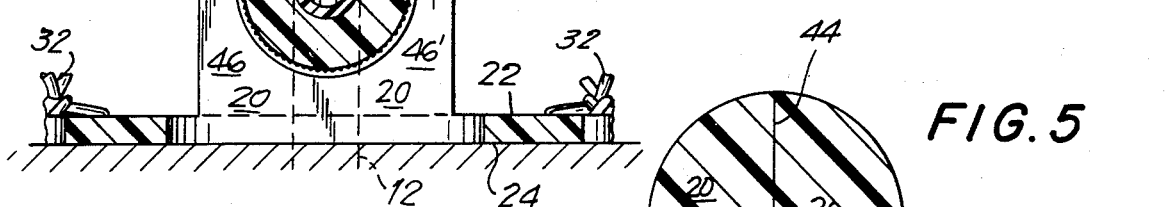
FIG. 4 is a cross-sectional view taken along line 4—4 of FIG. 2.
Figure 5:
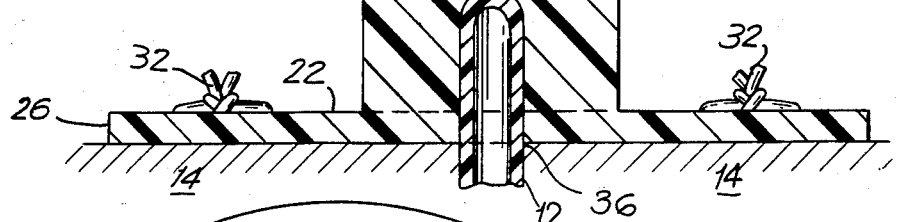
FIG. 5 is a cross-sectional view taken along line 5—5 of FIG. 2.
Figure 6:
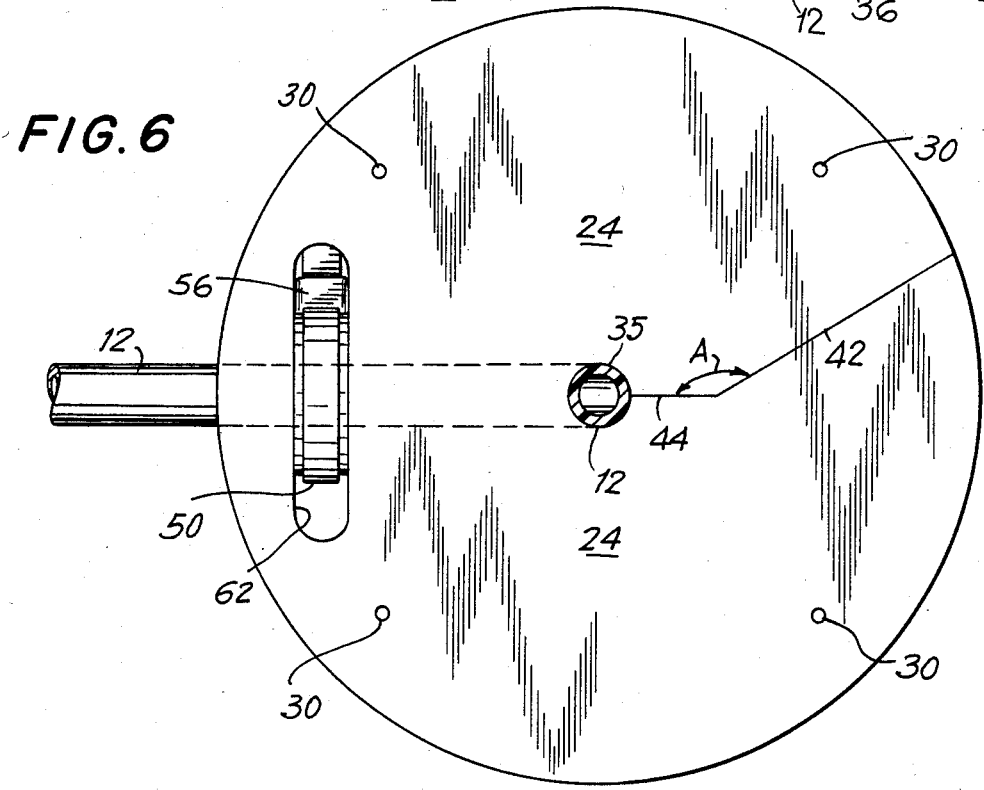
FIG. 6 is a bottom plan view of the device shown in FIG. 1 without sutures.

Referring now to the drawings wherein reference numeral 10 generally indicates a device in accordance with the present invention for anchoring a catheter tube 12 to the skin 14 of a patient. This device 10 includes a pad 16 having a thin circular disc-like base portion 18, and a body portion 20 extending therefrom. The base portion 18 includes a top surface 22, a flat bottom surface 24 and a peripheral edge 26 between and interconnecting the two surfaces. The body portion 20 extends or projects from the top surface 22 and has a perimetrical border or junction 28 with the top surface.

The pad 16 is preferably an integral piece composed of a resiliently flexible material such as an elastomer, e.g. silicone rubber. The thinness and flexibility of the pad 16 facilitates contouring of the flat bottom surface 20 to conform to the subjacent area of attachment on the patient's skin 14.

A plurality of spaced apart apertures 30 extending through the base portion 18 are located near the peripheral edge 26. These apertures 30 accommodate surgical sutures 32 which attach the device 10 to the patient's skin 14. Attachment can alternatively be achieved by using an adhesive applied to the bottom surface 24 of the pad 16. The adhesive can be exposed for use upon removal of a masking tape.

The pad 16 includes an internal arcuate passageway 34 with a first or entry port 36 centrally located in the base portion 18 and a second or exit port 38 located in the body portion 20 above the peripheral edge 26. The catheter tube 12 leaves the patient's skin 14, enters the first port 36 approximately normal to the bottom surface 24, and is redirected by the passageway 34 curvature so as to outlet approximately parallel to the bottom surface 24. This 90° change in the tubing direction is accomplished with a gentle curve in the passageway 34 so as to prevent the formation of a kink of crimp impeding the flow of fluids through the tube 12. When the tubing 12 is operably positioned, it extends from the patient's tissue, through the skin 14 and anchoring device 10 to a drainage bag or infusion container (not shown). A force connector (not shown) can be used, for example, to interconnect two lengths of tubing e.g. tubing passing through the anchoring device to tubing running from the drainage bag, or to interconnect the tubing and drainage bag, so as to release upon the application of undesired tension to the tubing.

The pad 16 has a continuous slit 40 which enables placement of the device 10 about the catheter tube 12 while the tube 14 is attached to the patient. The slit 40 includes two planar segments 42 and 44, which join at an angle A. The first slit segment 42 extends through the base 18 from the peripheral edge 26 of the pad 16 to the perimetrical border 28. The second slit segment 44 extends in the body portion 20 from the first port 36 to the second port 38, and in the base portion 18 from the perimetrical border 28 to the first port 36.

The second slit segment 44 penetrates through the body portion 20 so as to intersect and communicate with the arcuate passageway 34 along its entire length and effectively divide the body portion 20 into two symmetric lobes 46, 46'.

During installation of the anchoring device 10, the pad 16 is manually spread along the slit 40 and maneuvered over the puncture site where the catheter tubing 12 extends from the patient's skin 14. The spread apart first slit segment 42 is positioned so that the tubing 12 extends perpendicularly therethrough. The tubing 12 extending above the base portion 18 is pushed through the spread apart second slit segment 44 and into the curved passageway 34 so as to conform to the arcuate shape. Upon release of the pad so as to resiliently close the slit 40, the tube is frictionally held by the pad 16 within the passageway. The resilient closing of the slit 40 is facilitated by the angulated joining of the first and second slit segments 42 and 44, respectively. However, to further assure that the tubing 12 will not dislodge, the device 10 is provided with means for locking and unlocking the tubing 12 within the passageway 34.

The means for releasably locking the tubing includes an annular channel 48 grooved into the circumference of the body portion 20. The channel 48 accommodates an elongated cable tie 50 which, upon tightening, precludes the slit 40 from opening and causes the walls of the passageway to frictionally bear against the tubing 12, thereby preventing the tubing 12 from slipping through or from the passageway 34. The tie 50 has a free end 52 with a series of spaced apart transverse ridges 54 which is passed through a buckle 56. A pawl (not shown) extends from the buckle 56 and engages between the ridges 54. The pawl is angulated so as to permit tightening of the tie 50 above the body portion by pulling the free end 52 through the buckle 56, but prevents loosening since the ridges 54 prevent the angulated pawl from allowing the free end 52 of the tie 50 from moving in the opposite direction. Excess material at the free end 52 can be removed by snipping with a scissor. The tie 50 can be severed to permit removal of the tubing 12 from the passageway 34. Alternatively the pawl is constructed to be raised or lowered by a lever (not shown) on the buckle 56 permitting locking and unlocking of the pawl between the ridges 54. After proper placement of the anchoring device 10, sutures 32 can be applied to attach it to the patient's skin 14. The anchoring device 10 transfers load applied to the tubing 12 to the patient's skin 14, thereby greatly reducing the possibility of tubing dislodgement.

The base portion 18 is provided with a slot 62 proximate to the annular channel 48 so as to permit easy installation of the cable tie 50 about the body portion 20.

While the invention has been described above with respect to a specific embodiment, it should be clear that this embodiment is given by way of example and shall not be deemed as limiting the scope of the invention, except in accordance with the claims hereof.

I claim:

1. A device for anchoring a catheter tube or the like to the skin of a patient, comprising:

a resiliently flexible pad adapted for attachment to the skin of a patient, said pad including a disk-like base portion with a bottom surface for positioning subjacent to the patient's skin, a top surface having a body portion extending therefrom and a peripheral edge extending between said top and bottom surfaces;

said pad having an arcuate passageway therethrough predeterminedly dimensioned for snugly receiving the catheter tube therein, said passageway length extending from a first port in said base portion to a second port in said body portion, said body portion being supported by said base portion substantially throughout said passageway length, said pad having an elongated slot extending through said base portion from said peripheral edge to said first port and from said first port to said second port, said slit including a portion communicating along the entire length of said passageway, said pad being manually spreadable along said slit for permitting external accessibility to said passageway for placement of said passageway about said tube and resiliently closeable for frictionally restraining the tube therein; and means for releasably locking said slit in a closed position, said means including an annular channel grooved into said body portion extending transversely to said slit adapted to accommodate an elongated flexible tie insertable within said channel and tightenable about said body portion, said base portion having a slot proximate to said annular channel for facilitating insertion of said tie into said channel and about said body portion.

2. The device of claim 1 wherein said body portion has a perimetrical border with said base portion, said slit including a first and second segment, said first segment extending in said base portion from said peripheral edge to said border, said second segment extending in the base portion from said border to said first port and in said body portion from said first port to said second port, said first and second segments angularly joining so as to restrain said slit from spreading when in said resiliently closed position.

3. The device of claim 1 wherein said pad includes at least one aperture proximate to said peripheral edge of said pad for facilitating suturing of said pad to the patient's skin.

4. The device of claim 1 further comprising an elongate flexible tie inserted into said grooved annular channel.

* * * * *